(12) United States Patent
Clavel et al.

(10) Patent No.: US 10,842,648 B2
(45) Date of Patent: Nov. 24, 2020

(54) IMPLANT HOLDER

(71) Applicant: Biomet Manufacturing, LLC, Warsaw, IN (US)

(72) Inventors: Sebastien Clavel, Chateaudouble (FR); Jean-Michel Vizier, Mours (FR); Nicolas Brevet, Savigny (FR)

(73) Assignee: Biomet Manufacturing, LLC, Warsaw, IN (US)

( * ) Notice: Subject to any disclaimer, the term of this patent is extended or adjusted under 35 U.S.C. 154(b) by 160 days.

(21) Appl. No.: 15/557,204

(22) PCT Filed: Apr. 14, 2016

(86) PCT No.: PCT/US2016/027426
§ 371 (c)(1),
(2) Date: Sep. 11, 2017

(87) PCT Pub. No.: WO2016/168399
PCT Pub. Date: Oct. 20, 2016

(65) Prior Publication Data
US 2018/0049893 A1      Feb. 22, 2018

Related U.S. Application Data

(60) Provisional application No. 62/147,228, filed on Apr. 14, 2015.

(51) Int. Cl.
*A61B 17/58*      (2006.01)
*A61B 17/60*      (2006.01)
(Continued)

(52) U.S. Cl.
CPC .. *A61F 2/4609* (2013.01); *A61F 2002/30383* (2013.01); *A61F 2002/30398* (2013.01);
(Continued)

(58) Field of Classification Search
CPC ...... A61F 2002/4627; A61F 2002/4628; A61F 2002/4681; A61F 2002/30507
(Continued)

(56) References Cited

U.S. PATENT DOCUMENTS 5,098,437 A * 3/1992 Kashuba .............. A61F 2/4609
606/89
2004/0215200 A1 * 10/2004 Tornier ................. A61F 2/4609
606/91
(Continued)

FOREIGN PATENT DOCUMENTS

EP    2572679 A1     3/2013
EP    2572679 B1 *  7/2015
(Continued)

OTHER PUBLICATIONS

"European Application Serial No. 16721554.0, Communication Pursuant to Article 94(3) EPC dated Jun. 28, 2019", 4 pgs.
(Continued)

*Primary Examiner* — Jessica Weiss
(74) *Attorney, Agent, or Firm* — Schwegman Lundberg & Woessner, P.A.

(57) ABSTRACT

An impaction tip can be used in installing an implant. The impaction tip can comprise a body, and a sliding member. The body can have a handle-facing surface and an implant-facing surface. The body can define a grooved portion. The handle-facing surface can define an opening sized to receive a portion of an impaction handle. The sliding member can be located at least partially within the grooved portion. The sliding member can be slideable from an interior position to an exterior position. When the sliding member is in the exterior position a portion of the sliding member can contact the implant.

18 Claims, 8 Drawing Sheets

(51) Int. Cl.
*A61F 2/32* (2006.01)
*A61F 2/34* (2006.01)
*A61F 2/46* (2006.01)
*A61F 2/30* (2006.01)

(52) U.S. Cl.
CPC ............... *A61F 2002/30484* (2013.01); *A61F 2002/30507* (2013.01); *A61F 2002/4627* (2013.01); *A61F 2002/4628* (2013.01); *A61F 2002/4681* (2013.01)

(58) Field of Classification Search
USPC ............. 606/91, 86 R, 99; 623/22.11–22.12, 623/22.21
See application file for complete search history.

(56) References Cited

U.S. PATENT DOCUMENTS

| | | | | |
|---|---|---|---|---|
| 2010/0249857 | A1* | 9/2010 | Chana | A61F 2/4609 606/86 R |
| 2013/0079785 | A1* | 3/2013 | Burgi | A61F 2/4609 606/91 |

FOREIGN PATENT DOCUMENTS

| | | | | |
|---|---|---|---|---|
| WO | WO-2008099242 A1 | * | 8/2008 | ........... A61F 2/4609 |
| WO | WO-2008099242 A1 | | 8/2008 | |
| WO | WO-2009118673 A1 | * | 10/2009 | ......... A61F 2/30771 |
| WO | WO-2009118673 A1 | | 10/2009 | |
| WO | WO-2016168399 A2 | | 10/2016 | |
| WO | WO-2016168399 A3 | | 10/2016 | |

OTHER PUBLICATIONS

"Application Serial No. PCT/US2016/027426, Invitation to Pay Add'l Fees and Partial Search Report dated Jul. 25, 2016", 6 pgs.
"International Application Serial No. PCT/US2016/027426, International Search Report dated Oct. 5, 2016", 6 pgs.
"International Application Serial No. PCT/US2016/027426, Written Opinion dated Oct. 5, 2016", 8 pgs.
"European Application Serial No. 16721554.0, Response filed Sep. 4, 2018 to Office Action dated Feb. 22, 2018", 16 pgs.
"International Application Serial No. PCT/US2016/027426, International Preliminary Report on Patentability dated Oct. 26, 2017", 10 pgs.
"European Application Serial No. 16721554.0, Response filed Nov. 7, 2019 to Communication Pursuant to Article 94(3) EPC dated Jun. 28, 2019", 15 pgs.

* cited by examiner

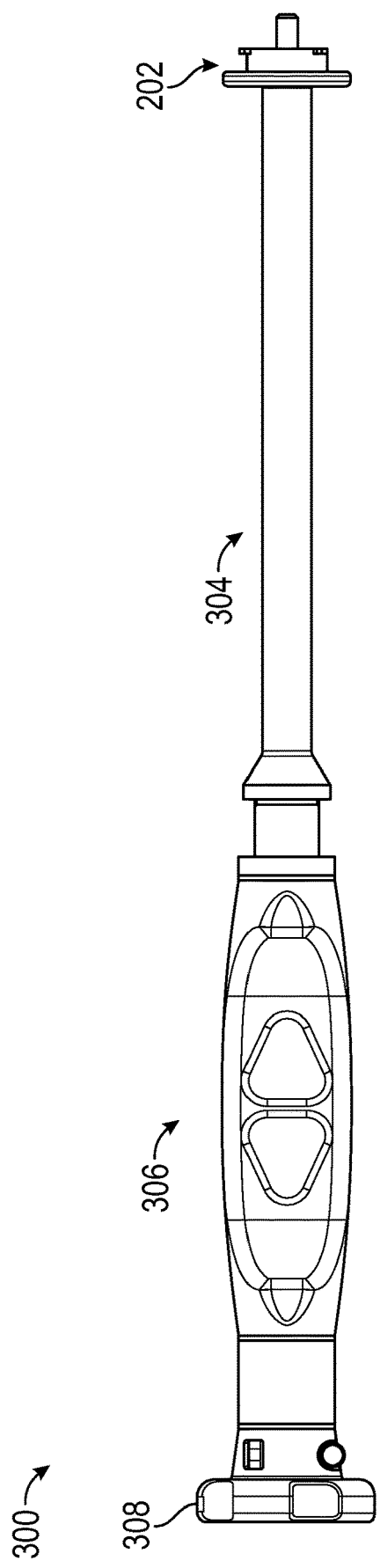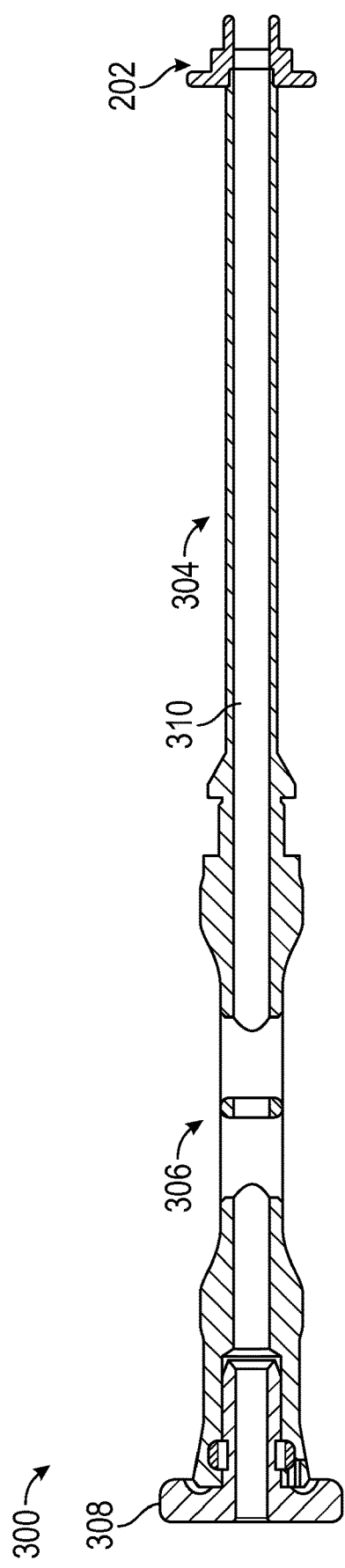

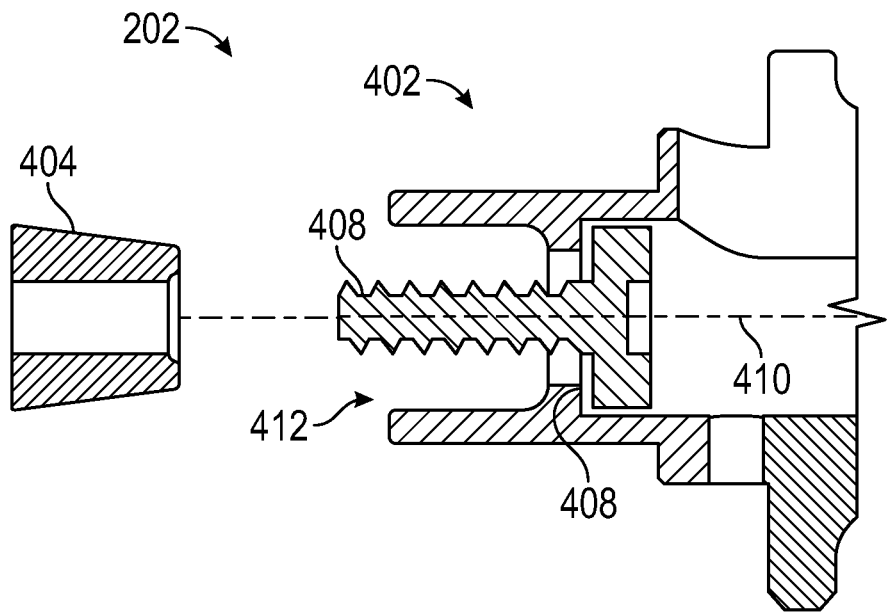
FIG. 4A
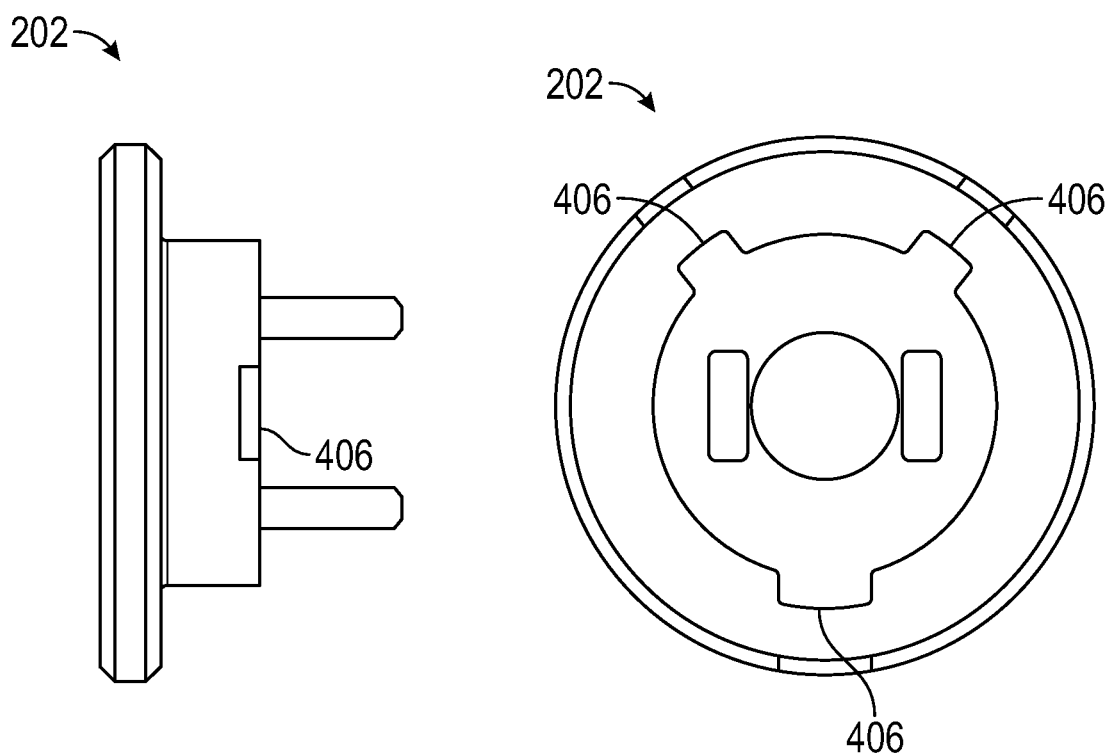
FIG. 4B
FIG. 4C

IMPLANT HOLDER

PRIORITY APPLICATIONS

This application is a U.S. National Stage Filing under 35 U.S.C. 371 from International Patent Application Serial No. PCT/US2016/027426, filed Apr. 14, 2016, published on Oct. 20, 2016 as WO 2016/168399A1, which application claims the benefit of priority to U.S. Patent Application No. 62/147,228, filed Apr. 14, 2015, the contents of which are hereby incorporated by reference in their entireties.

FIELD OF THE DISCLOSURE

The present disclosure relates to surgical implant systems, including implants, instruments, and methods for performing a hip arthroplasty.

BACKGROUND

A prosthesis can be positioned in an anatomy, such as a human patient, for various purposes. For example, a prosthesis can be positioned to replace an articulating portion of an anatomy. Incorrectly reamed anatomy can result in an incorrectly placed prosthesis. Incorrectly placed prostheses can result in pain, limit range of motion, increase wear debris, limit joint stability, and decrease the lifespan of the implant.

SUMMARY

To better illustrate the system disclosed herein, a non-limiting list of examples is provided here:

Example 1, can include an impaction tip for use in installing an implant. The impaction tip can comprise a body and a sliding member. The body can have a handle-facing surface and an implant-facing surface. The body can define a grooved portion. The handle-facing surface can define an opening sized to receive a portion of an impaction handle. The sliding member can be located at least partially within the grooved portion. The sliding member can also be slideable from an interior position to an exterior position. When the sliding member is in the exterior position a portion of the sliding member can contact the implant.

In Example 2, the impaction tip of Example 1 can optionally include the portion of the sliding member that contacts the implant including a curved surface that can be shaped to match an interior curved surface of the implant.

In Example 3, the impaction tip of any one of or any combination of Examples 1 and 2 can optionally include the implant-facing surface having a curved profile shaped to match a curved profile of the implant.

In Example 4, the impaction tip of any one of or any combination of Examples 1-3 can optionally include the body including a protrusion extending from an interior sidewall. The sliding member can define a notch sized to receive the protrusion.

In Example 5, the impaction tip of Example 4 can optionally include the protrusion defining a channel sized to allow a portion of the notch defined by the sliding member to pass through the channel.

In Example 6, the impaction tip of any one of or any combination of Examples 1-5 can optionally include a retaining pin sized to pass through a retaining pin hole defined by the body. The retaining pin can retain a second portion of the sliding member within the grooved portion.

In Example 7, the impaction tip of any one of or any combination of Examples 1-6 can optionally include the opening defined by the handle-facing surface including an indentation sized to receive a protrusion. The protrusion can extend from a connection tip of an impaction handle. The indentation and the protrusion can be configured to mate the impaction tip and the impaction handle.

In Example 8, the impaction tip of any one of or any combination of Examples 1-6 can optionally include the impaction handle being connected to the impaction tip at the handle-facing surface. The impaction handle can optionally include a translatable member located between the sliding member and a portion of the body. The translatable member can be configured to cause the sliding member to slide from the interior position to the exterior position.

In Example 9, the impaction tip of any one of or any combination of Examples 1-9 can optionally include a second sliding member located at least partially within the grooved portion. The second sliding member can be slideable from the interior position to a second exterior position such that a portion of the second sliding member contacts the implant.

Example 10 can include an impaction handle. The impaction handle can comprise a shaft, an impact head, a translatable member, and a connection tip. The shaft can extend from a first end to a second end. The impact head can be located at the first end. The connection tip can be located at the second end. A portion of the connection tip can be sized to pass through a hole defined by an impaction tip. The connection tip can define a through hole sized to allow a driver to pass through at least a portion of the connection tip. The translatable member can be located at a distal end of the connection tip. Rotation of the driver in a first direction can cause the translatable member to move towards the connection tip. Rotation of the driver in a second direction causes the translatable member to move away from the connection tip.

In Example 11, the impaction handle of Example 10 can optionally include the translatable member having a wedge shape with a narrow end proximate the distal end of the connection tip. The narrow end can be sized to pass into the through hole defined by the connection tip.

In Example 12, the impaction handle of any one of or any combination of Examples 10 and 11 can optionally include the connection tip including a protrusion extending from a circular portion of the connection tip. The protrusion can be configured to mate with an indentation defined by an impaction tip.

In Example 13, the impaction handle of Example 10 can optionally include the translatable member being configured to cause a plurality of sliding members of the impaction tip to grip a component of an implant.

In Example 14, the impaction handle of any one of or any combination of Examples 10-13 can optionally include the shaft being straight.

In Example 15, the impaction handle of Example 14 can optionally include the driver being located within the shaft and connected to the impact head such that rotation of the impact head can cause translation of the driver and movement of the translatable member.

In Example 16, the impaction handle of any one of or any combination of Examples 10-13 can optionally include the shaft being curved.

Example 17 can include a system for holding a hemispherical implant. The system can comprise an impaction handle and an impaction tip. The impaction handle can comprise a translatable member and a connection tip. The connection tip can define a through hole sized to allow a driver to pass through at least a portion of the connection tip. The translatable member can be located at a distal end of the connection tip. The impaction tip can comprise a body, a first sliding member, and a second sliding member. The body can have a handle-facing surface and an implant-facing surface. The body can define a grooved portion. The handle-facing surface can define an opening sized to receive the portion of the connection tip. The first sliding member can be located at least partially within the grooved portion. The first sliding member can be slideable from an interior position to a first exterior position. The second sliding member can be located at least partially within the grooved portion. The second sliding member can be slideable from the interior position to a second exterior position. The translatable member can be configured to cause the first sliding member and the second sliding member to move from the interior position to the first exterior position and the second exterior position, respectively, and contact the hemispherical implant.

In Example 18, the system of Example 17 can optionally include the implant-facing surface having a curved profile shaped to match a curved profile of the hemispherical implant.

In Example 19, the system of any one of or any combination of Examples 17 and 18 can optionally include the connection tip including a protrusion extending from a circular portion of the connection tip. The protrusion can be configured to mate with an indentation defined by the body of the impaction tip.

In Example 20, the system of any one of or any combination of Examples 17-19 can optionally include an impact head and a straight shaft. The straight shaft can connect the impact head and the translatable member. The driver can be located within the straight shaft and can be connected to the impact head such that rotation of the impact head causes movement of the translatable member.

In Example 21, the impaction tip, impaction, handle, or system of any one of or any combination of Examples 1-20 is optionally configured such that all elements or options recited are available to use or select from.

BRIEF DESCRIPTION OF THE FIGURES

The above-mentioned and other features and advantages of this invention, and the manner of attaining them, will become more apparent and the invention itself will be better understood by reference to the following description of embodiments of the invention taken in conjunction with the accompanying drawings, wherein:

FIGS. 3A and 3B show an example of an impaction handle in accordance with at least one example of the present disclosure.

FIGS. 4A-4C show an example of a connection tip in accordance with at least one example of the present disclosure.

Corresponding reference characters indicate corresponding parts throughout the several views. The exemplifications set out herein illustrate exemplary embodiments of the invention, and such exemplifications are not to be construed as limiting the scope of the invention any manner.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

Patients can suffer from various inflictions that can cause a need for a joint to be replaced. For example, a patient can suffer from arthritis or suffer an injury that can be repaired with a joint replacement. In one example, an acetabular cup can be positioned in an acetabulum of a patient to replace damaged or diseased bone.

The acetabular cup or other implant component can have a hemispherical shape and can be inserted into an acetabulum or other bone structure. To insert the implant, a surgeon can attach the implant to a handle. The handle can allow the surgeon the gain leverage for use in rotating or otherwise pivoting the implant. In addition, the handle can allow the surgeon to impact the implant with a mallet without damaging the implant.

As disclosed herein, an implant holder can include an impaction tip, an impaction handle, and an impact head. During use, the impaction tip can include a portion that expands to grip an implant. The handle can allow a surgeon to maneuver the implant and indirectly impact the implant to seat the implant into bone.

Figure 1A:
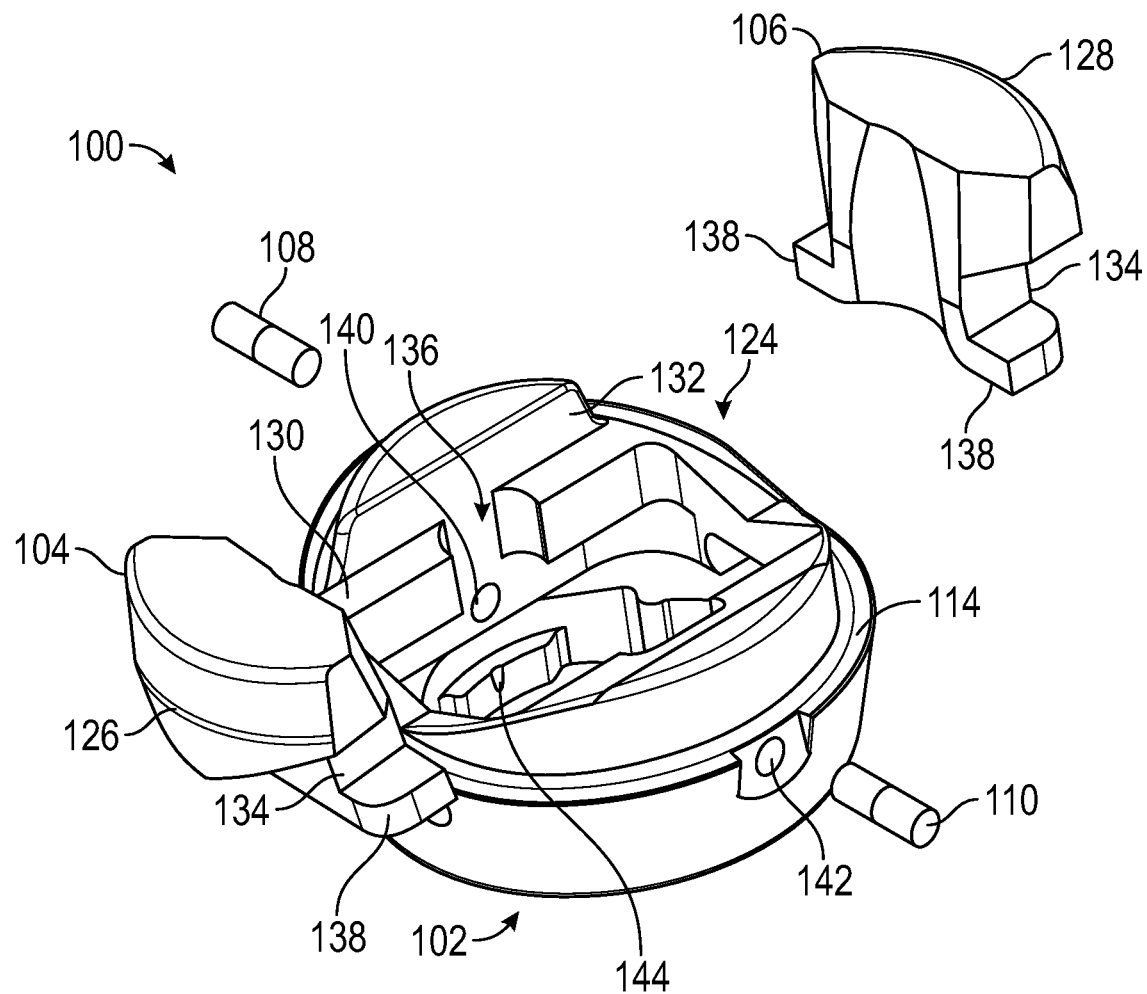
FIGS. 1A-1C show an example of an impaction tip in accordance with at least one example of the present disclosure.
Figure 1B:
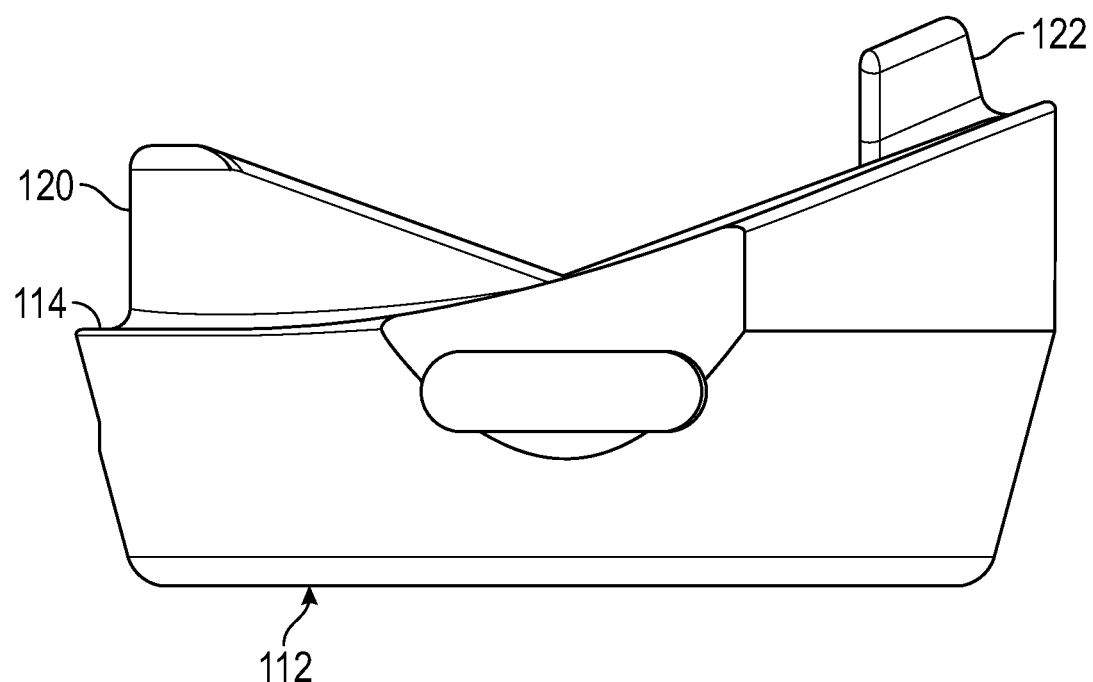
Figure 1C:
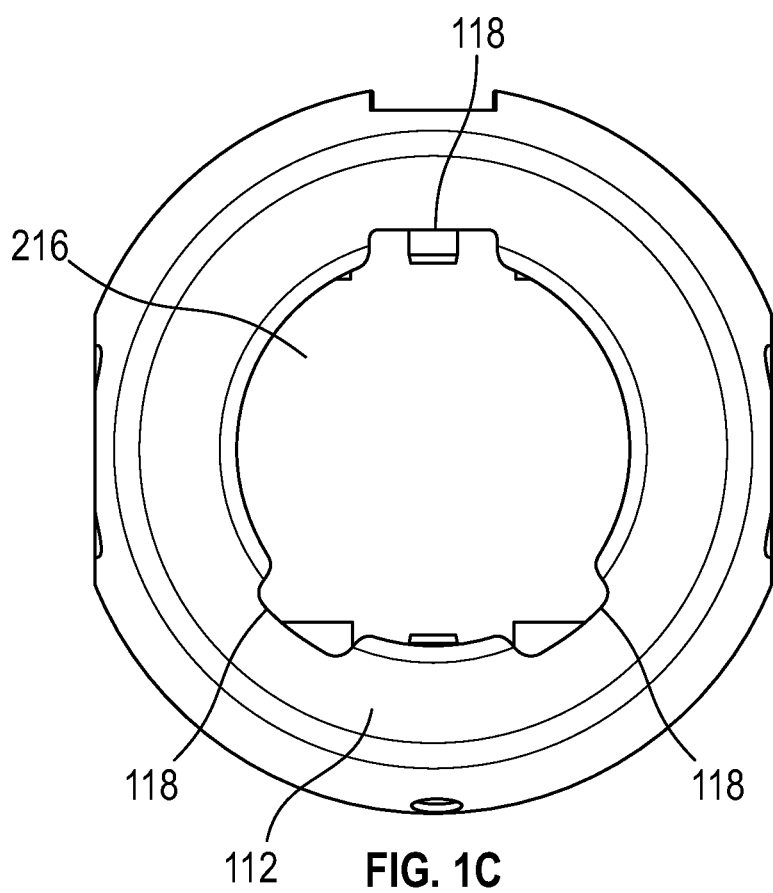

Turning now to the figures, FIGS. 1A-1C show an impaction tip 100 in accordance with at least one example of the present disclosure. The impaction tip 100 can include a body 102, a first sliding member 104, a second sliding member 106, a first pin 108, and a second pin 110. The body 102 can include a handle facing surface 112 and an implant facing surface 114. The handle facing surface 112 can define an opening 116 sized to receive a portion of a handle (e.g., an impaction handle 200 or an impaction handle 300 described below with respect to FIGS. 2A, 2B 3A, and 3B). The opening 116 can include one or more notches 118. The notches 118 can be spaced evenly about the opening 116. For example, three notches 118 can be spaced evenly every 120 degrees about the opening 116. In addition, the notches 118 can be spaced in a manner that would only allow the handle to be connected in one orientation. For example, two of the notches 118 can be spaced 150 degrees from a third notch 118.

The body 102 can include a first sidewall 120 and a second sidewall 122. The implant facing surface 114, the first sidewall 120, and the second sidewall 122 can allow an implant to be seated on the impaction tip 100. For example, the implant facing surface 114 can include a flat or curved profile that can match a profile of an implant. The first sidewall 120 and the second sidewall 122 can have a shape or profile that is similar to a portion of the implant. As a result, the implant can rest against the implant facing surface 114, the first sidewall 120, and the second sidewall 122 while the implant is being installed.

The body 102 can define a grooved portion 124 that can be parallel to the handle facing surface 112. A portion of the first sliding member 104 and a portion of the second sliding member 106 can be located within the grooved portion 124 and slide within the grooved portion 124. For example, the first sliding member 104 and the second sliding member 106 can slide from an interior position within the grooved portion 124 to a first exterior position and a second exterior position. The exterior positions can include a first curved surface 126 of the first sliding member 104 and a second curved surface 128 of the second sliding member 106 resting proximate a perimeter of the body 102 such that the first curved surface 126 and the second curved surface 128 can contact an inner surface of an implant. For example, the first curved surface 126 and the second curved surface 128 can be shaped to match a curvature of the inner surface of the implant.

The grooved portion 124 of the body 102 can include a protrusion 130. The protrusion 130 can extend from a sidewall 132 of the body 102. While FIG. 1A shows a single protrusion, a second protrusion can be located opposite the protrusion 130 within the grooved portion 124. During use, a recess 134 defined by the first sliding member 104 and the second sliding member 106 can slide around the protrusion 130. The protrusion 130 can define a channel 136. The channel 136 can allow a portion 138 of the first sliding member 104 and the second sliding member 106 to pass into the grooved portion 124 and secure the first sliding member 104 and the second sliding member 106 to the body 102.

The body 102 can define a first pin hole 140 and a second pin hole 142 sized to receive the first pin 108 and the second pin 110, respectively. The first pin 108 and the second pin 110 can pass through the sidewalls of the body 102 and limit movement of the first sliding member 104 and the second sliding member 106 such that the portion 138 of each cannot pass through the channel 136.

While FIGS. 1A-1C show two sliding members, any number of sliding members can be used. For example, one or more sliding members can be used to press against an implant and secure the implant to the connection tip 100.

The body 102, the first sliding member 104, the second sliding member 106, the first pin 108, and the second pin 110 can be manufactured from polymers, ceramics, metals, or any combination thereof. The body 102, the first sliding member 104, the second sliding member 106, the first pin 108, and the second pin 110 can be manufactured via various techniques including, but not limited to, injection molding, casting, machining, etc., or any combination thereof. For example, the body 102, the first sliding member 104, the second sliding member 106, the first pin 108, and the second pin 110 can be first injection molded and them machined using a computer numerically controlled (CNC) mill.

Figure 2A:
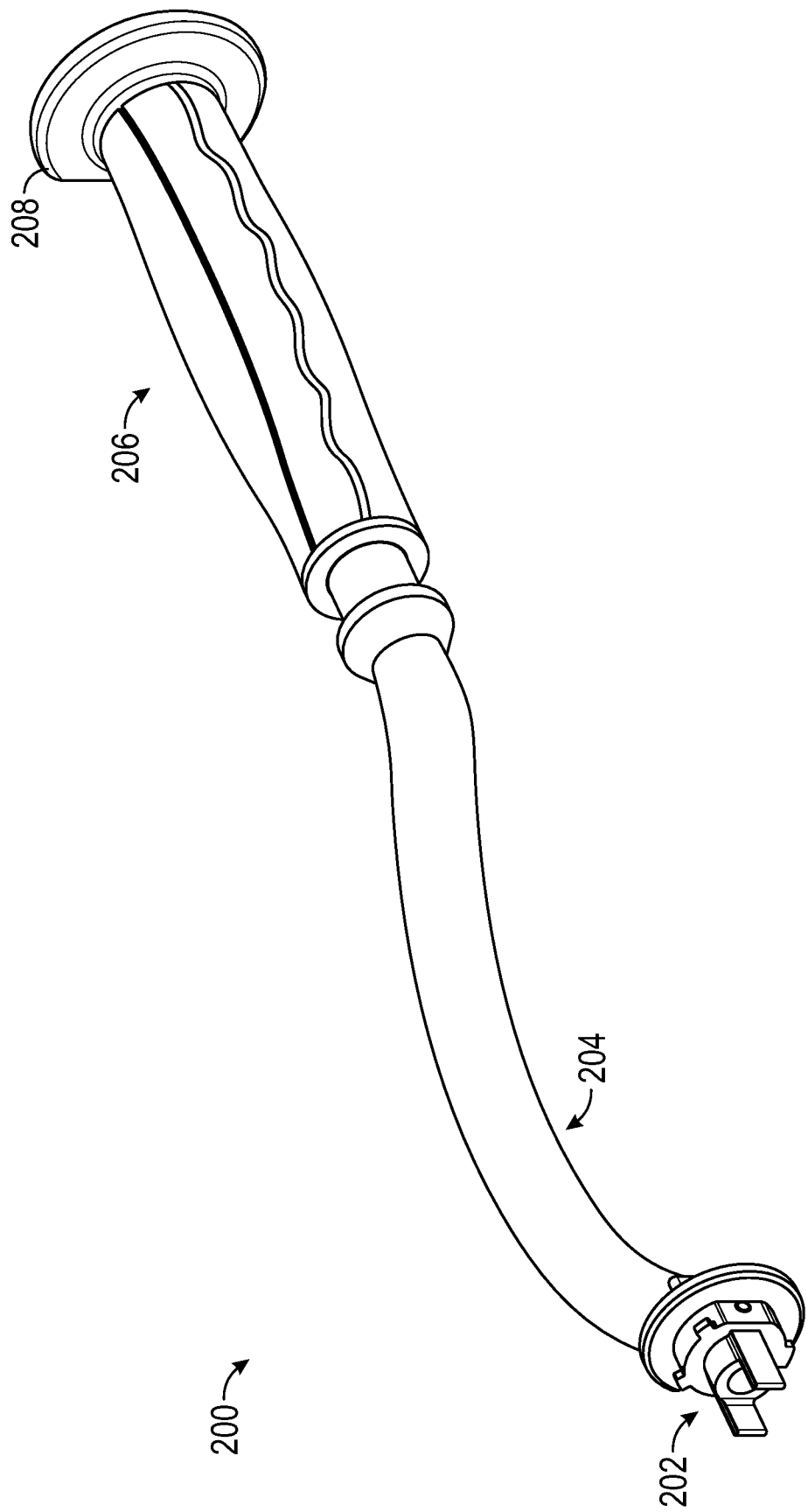
FIGS. 2A and-2B show an example of an impaction handle in accordance with at least one example of the present disclosure.
Figure 2B:
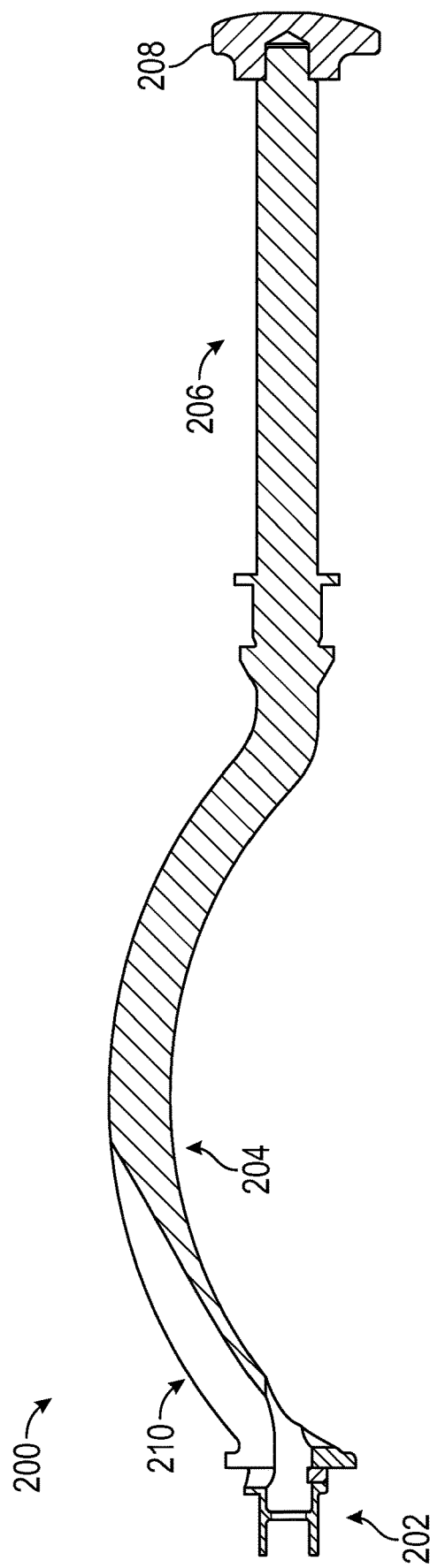

FIGS. 2A and 2B show an impaction handle 200 in accordance with at least one example of the present disclosure. The impaction handle 200 can include a connection tip 202, a shaft 204, a grip 206, and an impact head 208. As shown in FIGS. 2A and 2B, the shaft 204 of the impaction handle 200 can extend from a first end to a second end and can be curved. The curved profile of the shaft 204 can facilitate orienting the implant during a procedure. For example, during a hip replacement, the curved profile of the shaft 204 can facilitate inserting a hemispherical cup into an acetabulum of a hip joint. For instance, when a patient is in an anterior supine position, the curved profile of the shaft 204 can allow the surgeon to position the hemispherical cup from a horizontal angle without having to reposition the patient or other instruments within the surgical environment.

The shaft 204 can include a through hole 210 located proximate the first end of the shaft 204. As discussed below with regards to FIGS. 6A-6C, the through hole 210 can allow a driver 504 to pass through a portion of the shaft 204 and the connection tip 202. The shaft 204 can be manufactured from metals, polymers, ceramics, or any combination thereof. The shaft 204 can be manufactured using a variety of techniques including, but not limited to, machining, injection molding, casting, etc., or any combination thereof.

The grip 206 can allow a surgeon to grip the impaction handle 200. The grip 206 can be contoured for an ergonomic feel. The grip 206 can be manufactured from metals, polymers, ceramics, or any combination thereof. The grip 206 can be manufactured using a variety of techniques including, but not limited to, machining, injection molding, overmolding, casting, etc., or any combination thereof The impact head 208 can be located at the second end of the shaft 204 and can be a continuation of the shaft 204 or the grip 206. The impact head 208 can provide a location for a surgeon to strike the impaction handle 200 during a surgery to seat an implant. The impact head 208 can be manufactured from metals, polymers, ceramics, or any combination thereof. The impact head 208 can be manufactured from a variety of techniques including, but not limited to, machining, injection molding, casting, etc., or any combination thereof.

FIGS. 3A and 3B show an alternative impaction handle 300 in accordance with at least one example of the present disclosure. The impaction handle 300 can include the connection tip 202, a shaft 304, a grip 306, and an impact head 308. As shown in FIGS. 3A and 3B, the shaft 304 of the impaction handle 300 can extend from a first end to a second end and can be straight. The straight profile of the shaft 304 can facilitate orienting the implant during a procedure. For example, during a hip replacement, the straight profile of the shaft 304 can facilitate inserting a hemispherical cup into an acetabulum of a hip joint. For instance, when a patient is positioned for posterior insertion of the hemispherical cup into the acetabulum, a straight impaction handle, such as impaction handle 300 can provide a surgeon with greater leverage and minimize deflections when the impact head 308 is struck with a mallet.

The shaft 304 can include a through hole 310 that can extend from the connection tip 202 to the impact head 308. As discussed below with regards to FIGS. 6A-6C, the through hole 310 can allow a threaded rod to pass through the shaft 304, the grip 306, and at least a portion of the impact head 308. The shaft 304 can be manufactured from metals, polymers, ceramics, or any combination thereof. The shaft 304 can be manufactured using a variety of techniques including, but not limited to, machining, injection molding, casting, etc., or any combination thereof.

The grip 306 can allow a surgeon to grip the impaction handle 300. The grip 306 can be contoured for an ergonomic feel. The grip 306 can be manufactured from metals, polymers, ceramics, or any combination thereof. The grip 306 can be manufactured using a variety of techniques including, but not limited to, machining, injection molding, overmolding, casting, etc., or any combination thereof.

The impact head 308 can be located at the second end of the shaft 304. The impact head 308 can provide a location for a surgeon to strike the impaction handle 300 during a surgery to seat an implant. The impact head 308 can rotate about a centerline of the through hole 310. As discussed below with regard to FIGS. 6A-6C, rotation of the impact head 308 can cause the first sliding member 104 and the second sliding member 106 to travel from the interior position to the first and second exterior positions, respectively.

The impact head 308 can be manufactured from metals, polymers, ceramics, or any combination thereof. The impact head 308 can be manufactured using a variety of techniques including, but not limited to, machining, injection molding, casting, etc., or any combination thereof.

FIGS. 4A-4C show an example of the connection tip 202. As shown in FIG. 4A, the connection tip can include a tip portion 402 and a translatable member 404 located at a distal end of the connection tip 202. The tip portion 402 can include a plurality of protrusions 406 that extend from a circular portion of the connection tip 202. The protrusions 406 can be of different sizes and spaced such that the protrusions 406 line up with the notches 118 defined in the impaction tip 100. During use, the protrusions 406 can pass through the notches 118 and the impaction tip 100 can be rotated about a centerline 410 of the connection tip 202. The rotation of the impaction tip 100 can cause the protrusions 406 to rest upon lugs 144 defined by the body 102 of the impaction tip 100. The lugs 144 can include depressions or other features to secure the impaction tip 100 to the connection tip 202. For example, a recess defined by the lugs 144 can be slightly smaller than the protrusions 406 such that friction between the protrusions 406 and the surfaces of the lugs 144 and the body 102 hinder movement of the impaction tip 100.

The connection tip 202 can include a bolt 408. The head of the bolt 408 can rest against a surface 410 of the connection tip 202 and the threaded portion of the bolt 408 can pass through the connection tip 202. The threaded portion of the bolt 408 can engage the translatable member 404 such that rotation of the bolt 406 can cause the translatable member 404 to travel along the centerline 410. For example, rotation of the bolt 408 in a clockwise direction can cause the translatable member 404 to travel towards an opening 412 of the connection tip 202. All or a portion of the translatable member 404 can fit into the opening 412.

Figure 6C:
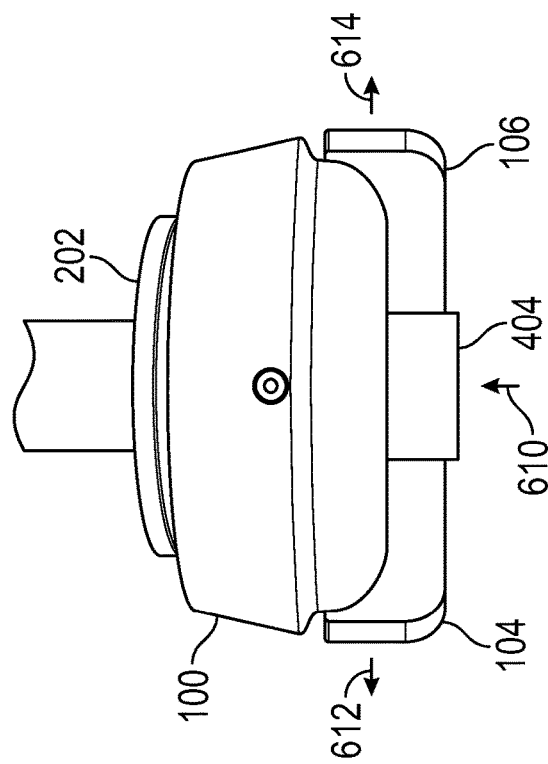
FIGS. 6A-6C show an example illustration of a method of attaching an implant to an implant holder in accordance with at least one example of the present disclosure.

The translatable member 404 can have a wedge or conical shape. During use, and as shown in FIG. 6C, as the translatable member 404 is moved towards the connection tip 202, exterior surfaces of the translatable member 404 can contact the first sliding member 104 and the second sliding member 106. Due to the wedge or conical shape of the translatable member 404, the contact between the exterior surface of the translatable member 404 and the first sliding member 104 and the second sliding member 106 can cause the first sliding member 104 and the second sliding member 106 to slide from the interior position to the first and second exterior positions as described herein. For example, the translatable member 404 can have a polished exterior surface to reduce friction between the translatable member 404 and the first sliding member 104 and the second sliding member 106.

As the first sliding member 104 and the second sliding member 106 move from the interior position to the first exterior position and the second exterior position, respectively, the first curved surface 126 and the second curved surface 128 can contact an interior surface of an implant. The contact between the first curved surface 126, the second curved surface 128, and the implant can cause the impaction tip 100 to hold the implant via a surface friction force. Stated another way, the translatable member 404 wedges between the first sliding member 104 and the second sliding member 106 causing the first curved surface 126 and the second curved surface 128 to grip the implant. To prevent damage to the implant, the first curved surface 126 and the second curved surface 128 can deform to conform to the surface of the implant.

While FIG. 4A shows the bolt 408 can be accessed via the through hole 210 of the impaction handle 200, a threaded rod can pass through the straight impaction handle 300. The threaded rod can be connected to the impact head 308 such that rotation of the impact head 308 causes the threaded rod to rotate. The threaded rod can be connected directly to the impact head 308 or can be a bolt that passes through the impact head 308. For example, the impact head 308 can include a hexagonal recess that can receive a head of a long bolt that passes through the impact head 308, the shaft 304, and into or through the connection tip 202.

The connection tip 202 can be a continuation of the shaft 204 or 304. For example, the shaft 204 can be made of surgical grade stainless steel and during the manufacturing process of the shaft 204 to connection tip 202 can be milled using a CNC machine at the same time the shaft 204 is formed.

Figure 5:
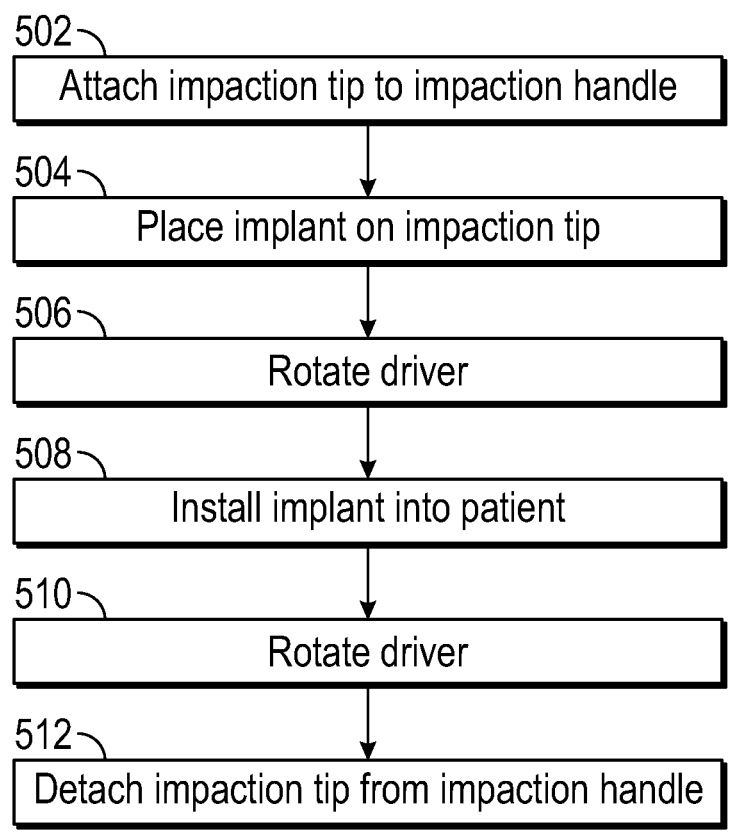
FIG. 5 shows an example method for attaching and detaching an implant to an impaction tip in accordance with at least one example of the present disclosure.

FIG. 5 shows a flowchart for a method 500 of attaching and detaching an implant to the impaction tip 100. The method 500 is being described with reference to the impaction tip 100, the impaction handles 200 and 300, the connection tip 202, the impact heads 208 and 308, and other components described herein merely for purposes of example. The method 500 is not limited to the particular components mentioned in discussing FIG. 5 or particular structures thereof. In addition, FIG. 5 will be discussed in conjunction with FIGS. 6A-6C to illustrate the method 500.

The method 500 can begin at stage 502 where the impaction tip 100 is connected to the impaction handle 200 or 300. As disclosed herein, the impaction tip 100 can connect to the impaction handle 200 or 300 via the connection tip 202. The protrusions 406 can pass through the opening 116 and the notches 118. Rotation of the impaction tip 100 relative to the impaction handle 200 or 300 can secure the impaction tip 100 to the connection tip 202.

Figure 6B:
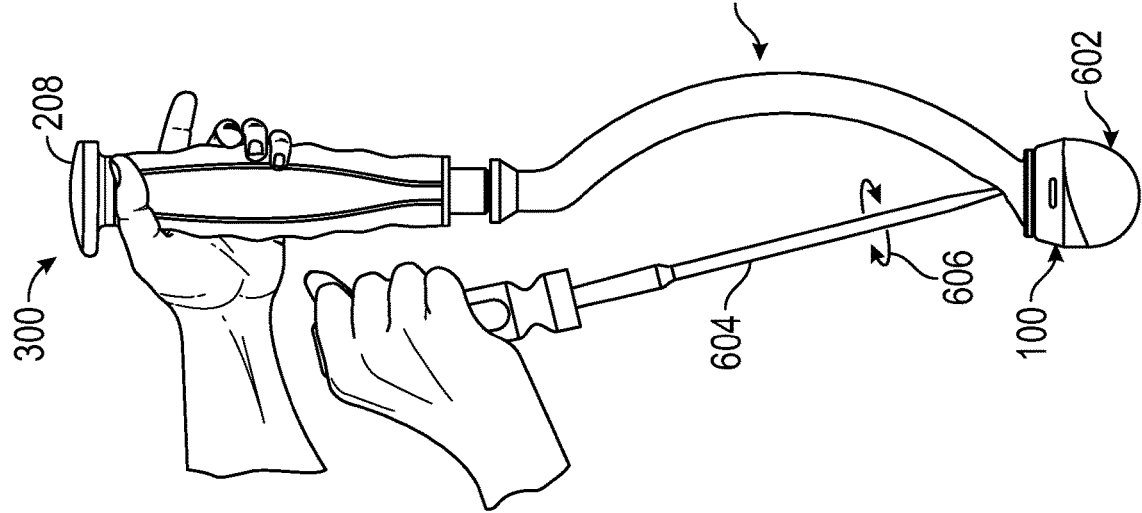
Figure 6A:
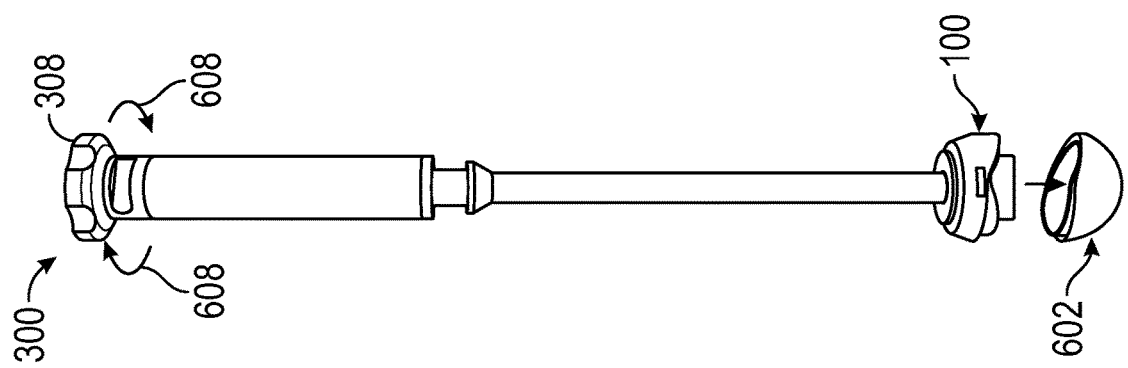

The impaction tip 100 can be selected from a plurality of impaction tips. For example, the impaction tip 100 can be included in a system of surgical components and the surgeon can select the appropriate impaction tip for a given implant. For instance, the surgeon may select an impaction tip having a diameter of 44 mm for use with a hemispherical cup having an inside diameter of 50 mm. While FIG. 6A shows impaction handle 300, impaction handle 200 could be used in place of impaction handle 300.

From stage 502 the method 500 can proceed to stage 504 where an implant 602 can be placed on the impaction tip 100. As shown in FIG. 6A, the implant facing surface 114 can be placed in contact with the implant 602. From stage 504 the method 500 can proceed to stage 506 where a driver 604 can be rotated. For example, as shown in FIG. 6B, the bolt 408 can be rotated with the driver 604. For instance, the driver 604 can be rotated in a clockwise or counterclockwise direction as indicated by arrows 606. While FIG. 6B shows the impaction handle 200, the impaction handle 300 could be used in place of the impaction handle 200. For example, a straight handle may be needed for a given surgical procedure and after connecting the impaction tip 100 to the impaction handle 300 and placing the implant 602 on the impaction tip 100, the impact head 308 can be rotated as indicated by arrows 608 as shown in FIG. 6A and as disclosed herein.

FIG. 6C shows the effect of rotation of the driver 604 or the impact head 308. For simplicity, FIG. 6C will be described in terms of rotating the driver 604. As shown in FIG. 6C, rotation of the driver 604 can cause the translatable member 404 to travel towards the connection tip 202 as indicated by arrow 610. Due to the shape of the translatable member 404, as the translatable member 404 travels towards the connection tip 202, the first sliding member 104 and the second sliding member 106 can travel in a direction transverse to the movement direction of the translatable member 404 as indicated by arrows 612 and 614, respectively. As the first sliding member 104 and the second sliding member 106 travel, they can contact an inner surface of the implant 602 as disclosed herein.

The surfaces of the impaction tip 100 that contact the implant can be made of a deformable material such that the contact does not damage the implant. For example, the first curved surface 126, the second curved surface 128, and the implant facing surface 114 that contact the implant 602 can be made of a polymer that will deform so as to not scratch, dent, bend, or otherwise alter the implant 602 or a surface finish of the implant 602.

From stage 506 the method 500 can proceed to stage 508 where the implant 602 can be installed in the patient. For example, the implant 602 can be installed in an acetabulum of a patent. If needed, the surgeon can strike the impact head 208 or 308 with a mallet to seat the implant 602.

From stage 506 the method 500 can proceed to stage 510 where the driver 606 can be rotated. For example, if the driver 606 was rotated clockwise in stage 506 to attach the implant 602 to the impaction tip 100, the driver 606 can be rotated counterclockwise in stage 510 to release the implant 602 from the impaction tip 100.

From stage 510 the method 500 can proceed to stage 512 where the impaction tip 100 can be detached from the impaction handle 200 or 300. Removing the impaction tip 100 from the impaction handle 200 or 300 can allow for the impaction tip 100, impaction handles 200 and 300 to be cleaned and sterilized for reuse with other patients.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

What is claimed is:

1. An impaction tip for use in installing an implant, the impaction tip comprising:
   a body having a handle-facing surface and an implant-facing surface located opposite the handle-facing surface, the body defining a grooved portion, the handle-facing surface defining an opening sized to receive a portion of an impaction handle; and
   a sliding member located at least partially within the grooved portion and slideable from an interior position to an exterior position,
   wherein when the sliding member is in the exterior position a portion of the sliding member contacts the implant, and
   wherein the implant-facing surface comprises a peripheral portion that has a slope complimentary to a surface of the implant.

2. The impaction tip of claim 1, wherein the portion of the sliding member that contacts the implant includes a curved surface shaped to match an interior curved surface of the implant.

3. The impaction tip of claim 1, wherein the body includes a protrusion extending from an interior sidewall and the sliding member defines a notch sized to receive the protrusion.

4. The impaction tip of claim 3, wherein the protrusion defines a channel sized to allow a portion of the notch defined by the sliding member to pass through the channel.

5. The impaction tip of claim 1, further comprising a retaining pin sized to pass through a retaining pin hole defined by the body and retain a second portion of the sliding member within the grooved portion.

6. The impaction tip of claim 1, wherein the opening defined by the handle-facing surface includes a plurality of indentations, each of the indentations sized to receive a respective protrusion extending from a connection tip of the impaction handle, the plurality of indentations and the respective protrusion configured to mate the impaction tip and the impaction handle.

7. The impaction tip of claim 1, further comprising the impaction handle connected to the impaction tip at the handle-facing surface, the impaction handle including a translatable member located between the sliding member and a portion of the body and configured to cause the sliding member to slide from the interior position to the exterior position.

8. The impaction tip of claim 1, further comprising a second sliding member located at least partially within the grooved portion and slideable from the interior position to a second exterior position such that a portion of the second sliding member contacts the implant.

9. An impaction handle comprising:
   a shaft extending from a first end to a second end;
   an impact head located at the first end;
   a translatable member; and
   a connection tip located at the second end and a portion of the connection tip sized to pass through a hole defined by an impaction tip, the connection tip including a plurality of protrusions extending from a circular portion of the connection tip, the plurality of protrusions spaced about the circular portion so as to line up with corresponding notches defined by the impaction tip; the connection tip defining a through hole sized to allow a driver to pass through at least a portion of the connection tip, the translatable member located at a distal end of the connection tip,
   wherein:
      rotation of the driver in a first direction causes the translatable member to move towards the connection tip and at least partially into an opening defined by the connection tip, and
      rotation of the driver in a second direction causes the translatable member to exit the opening defined by the connection tip and move away from the connection tip.

10. The impaction handle of claim 9, wherein the translatable member has a wedge shape with a narrow end proximate the distal end of the connection tip; the narrow end sized to pass into the through hole defined by the connection tip.

11. The impaction handle of claim 9, wherein the translatable member is configured to cause a plurality of sliding members of the impaction tip to grip a component of an implant.

12. The impaction handle of claim 9, wherein the shaft is straight.

13. The impaction handle of claim 12, wherein the driver is located within the shaft and connected to the impact head such that rotation of the impact head causes rotation of the driver and movement of the translatable member.

14. The impaction handle of claim 9, wherein the shaft is curved.

15. The impaction handle of claim 9, wherein each of the plurality of protrusions is spaced apart from a distal surface of the connection tip.

16. A system for holding a hemispherical implant, the system comprising:
an impaction handle comprising:
a translatable member, and a connection tip, the connection tip defining a through hole sized to allow a driver to pass through at least a portion of the connection tip, the translatable member located at a distal end of the connection tip; and
an impaction tip comprising:
a body having a handle-facing surface and an implant-facing surface located opposite the handle-facing surface, the body defining a grooved portion, the handle-facing surface defining an opening sized to receive the portion of the connection tip;
a first sliding member located at least partially within the grooved portion and slideable from an interior position to a first exterior position; and
a second sliding member located at least partially within the grooved portion and slideable from the interior position to a second exterior position,
wherein the implant-facing surface comprises an outermost peripheral portion that has a slope complimentary to a surface of the implant, and
wherein the translatable member is configured to cause the first sliding member and the second sliding member to move from the interior position to the first exterior position and the second exterior position, respectively, and contact the hemispherical implant.

17. The system of claim 16, wherein the connection tip includes a plurality of protrusions extending from a circular portion of the connection tip, each of the plurality of protrusions configured to mate with a respective indentation defined by the body of the impaction tip.

18. The system of claim 16, further comprising:
an impact head; and
a straight shaft connecting the impact head and the translatable member, the driver located within the straight shaft and connected to the impact head such that rotation of the impact head causes movement of the translatable member.

* * * * *

UNITED STATES PATENT AND TRADEMARK OFFICE
CERTIFICATE OF CORRECTION

PATENT NO. : 10,842,648 B2
APPLICATION NO. : 15/557204
DATED : November 24, 2020
INVENTOR(S) : Clavel et al.

Page 1 of 1

It is certified that error appears in the above-identified patent and that said Letters Patent is hereby corrected as shown below:

In the Claims

In Column 10, Line 35, in Claim 9, delete "tip;" and insert --tip,-- therefor

In Column 10, Line 50, in Claim 10, delete "tip;" and insert --tip,-- therefor

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*